United States Patent [19]
Harris

[11] Patent Number: 5,876,361
[45] Date of Patent: Mar. 2, 1999

[54] EXERCISE AND POSTURE CORRECTING DEVICE

[76] Inventor: James A. Harris, 24605 S. River Trail, Channahon, Ill. 60410

[21] Appl. No.: 997,511

[22] Filed: Dec. 23, 1997

[51] Int. Cl.[6] ........................................................ A61F 5/00
[52] U.S. Cl. ................................................................ 602/19
[58] Field of Search ............................. 602/19; 482/121, 482/122, 124, 127; 2/44, 45, 92

[56] References Cited

U.S. PATENT DOCUMENTS

| | | | |
|---|---|---|---|
| 199,463 | 1/1878 | Partridge | 602/19 |
| 2,760,486 | 8/1956 | Ward | 602/19 |
| 2,835,247 | 5/1958 | Stabholc | 602/19 |
| 2,906,260 | 9/1959 | Myers | 602/19 |
| 3,162,441 | 12/1964 | Karlik | 482/121 |
| 4,541,419 | 9/1985 | Osawa | 602/19 |
| 5,199,940 | 4/1993 | Morris et al. | 602/19 |
| 5,584,799 | 12/1996 | Gray | 602/19 X |
| 5,651,764 | 7/1997 | Chiu | 602/19 X |
| 5,685,831 | 11/1997 | Ffloyd | 602/19 |

Primary Examiner—Linda C. M. Dvorak
Attorney, Agent, or Firm—Ernest Kettelson

[57] ABSTRACT

An exercise and posture correcting device comprising a slightly bowed strip of spring steel or other material having comparable flexing characteristics extends upwardly from the rearward portion of a broad width waist belt to which it is connected at one end to a padded contact member connected to a height adjustable extension sleeve slidably received on the strip at its upper end, such padded contact member at such upper end being positioned to bear against the wearer's back in the region between his shoulder blades. The padded contact member is biased toward and against the wearer's back by the strip of spring steel or other material. A rigid plate is secured to the broad width waist belt in back on which a tension adjusting ratchet assembly is mounted to increase or decrease pressure against the user's back as desired.

16 Claims, 4 Drawing Sheets

EXERCISE AND POSTURE CORRECTING DEVICE

FIELD OF THE INVENTION

This invention relates to the field of exercise devices to strengthen muscles of the human body, and in particular those that strengthen the muscles which enable a person to maintain good posture when standing.

BACKGROUND OF THE INVENTION

Prior art devices in this general field of which the inventor is aware include those disclosed in the following United States Patent, copies of which are readily available to the public: No. 5,342,289; No. 5,199,940; No. 4,995,383; No. 5,107,826; No. 5,086,757; No. 4,640,269; No. 3,420,230; No. 2,871,650; No. 1,755,641; No. 1,722,192; No. 1,581,791; No. 1,410,056; No. 639,072; No. 443,764. The exercise and posture correcting device in accordance with the present invention are an improvement over the prior art in that it provides a light weight unit which can be worn by the user for relatively long periods of time as he goes about his business and carries on his regular activities, to continuously provide the muscle stimulation and exercise needed by the muscles which enable a person to maintain good posture over a relatively lengthy sustained time period. The present invention can be worn and continuously used for several hours or more. If desired it can be used and worn all day. Stimulation and exercise of the relevant muscles over a lengthy sustained period of time is more successful in achieving the desired result as compared to exercise and posture devices that can only be used on a sustained continuous basis no more than an hour or less.

SUMMARY OF THE INVENTION

The exercise and posture correcting device in accordance with the present invention comprises a relatively broad width waist belt for the user to secure around his waist and an elongated tensioning member of spring steel or the like extending upward from the back side of the belt to bias a padded contact member against the back of the user in the region between his shoulder blades. On the back side of the belt, a metal plate is riveted or otherwise secured to the belt. A ratchet assembly is mounted on the metal plate, and the lower end of the elongated tensioning member is secured to the rotatable shaft of the ratchet assembly. A pair of knobs are provided, one on each opposite end of the rotatable shaft to enable the user who is wearing the belt to reach behind and rotate the shaft. When rotated in one direction, the tensioning member is caused to increase the bias of the padded contact member against the back of the user. The ratchet assembly permits rotation in such direction but blocks rotation in the opposite direction until the pawl of the ratchet assembly is disengaged from the ratchet teeth on the rotatable shaft. The user can adjust the amount of pressure or bias of the padded contact member against his back by using the knobs to rotate the shaft in the bias increasing direction and by using the pawl release member of the ratchet assembly together with one or both knobs to rotate the shaft in the opposite bias decreasing direction.

The lower portion of the spring steel tensioning member includes a coiled portion extending around the rotatable shaft inwardly from the lower end connected to the rotatable shaft. The tensioning member includes a slightly arcuate or slightly bowed portion extending upwardly from the coiled section toward the padded contact member. The padded contact member is connected to a height adjusting sleeve mounted on the upper end of the spring steel strip portion of the tensioning member to slide up or down thereon. The height of the contact member can thus be adjusted to reach the proper position between the shoulder blades of users of different heights.

Further description and advantages of the exercise and posture correcting device in accordance with this invention will become apparent from the more detailed description which follows and from the accompanying drawings.

DESCRIPTION OF PREFERRED EMBODIMENT

Figure 1:
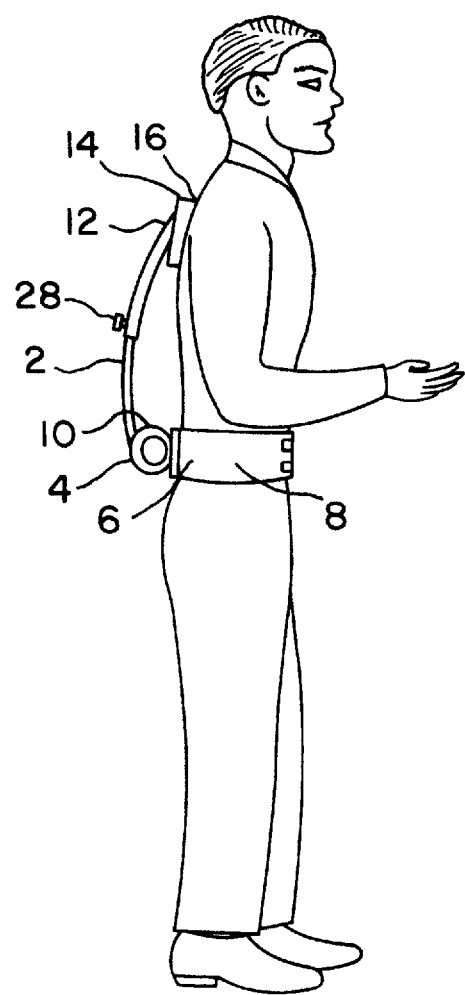
FIG. 1 is an elevation view of an exercise and posture correcting device in accordance with this invention shown in place on a user.
Figure 2:
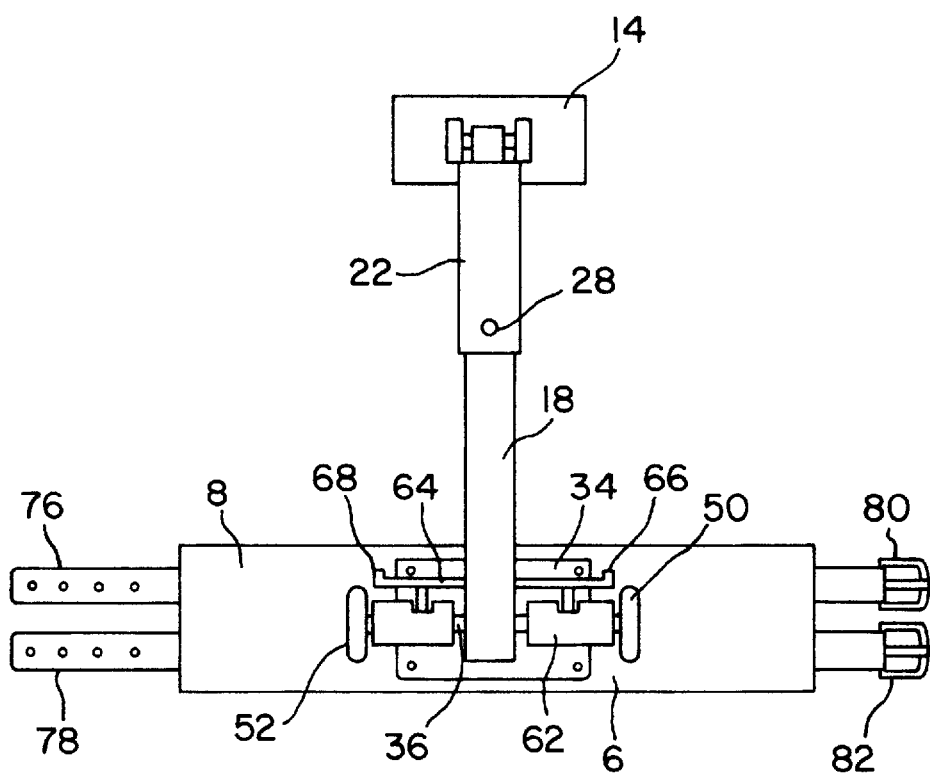
FIG. 2 is an elevation view from the rear of the exercise and posture correcting device in accordance with this invention.
Figure 3:
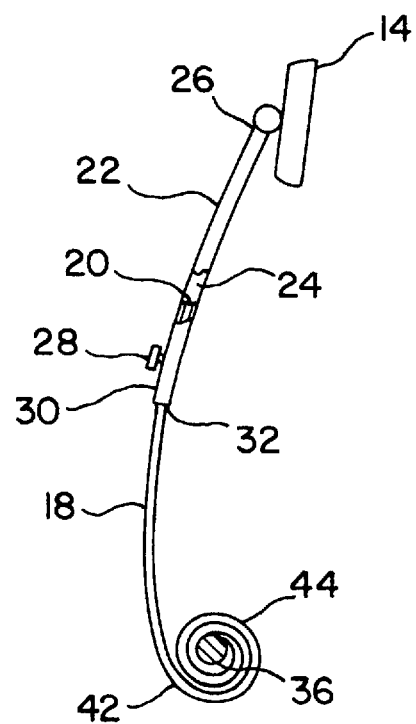
FIG. 3 is a somewhat enlarged view of the elongated biasing member of the exercise and posture correcting device, illustrating the lower spring steel strip received in a height adjusting sleeve, a portion of its side wall broken away to show the upper end of the steel strip received therein.
Figure 4:
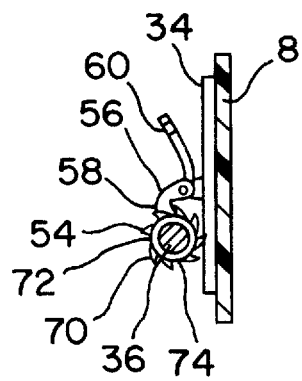
FIG. 4 is a section view of the tension adjusting ratchet assembly to illustrate the ratchet teeth on the adjusting shaft, the position of the pawl as it engages the ratchet teeth, and the pawl release lever.
Figure 5:
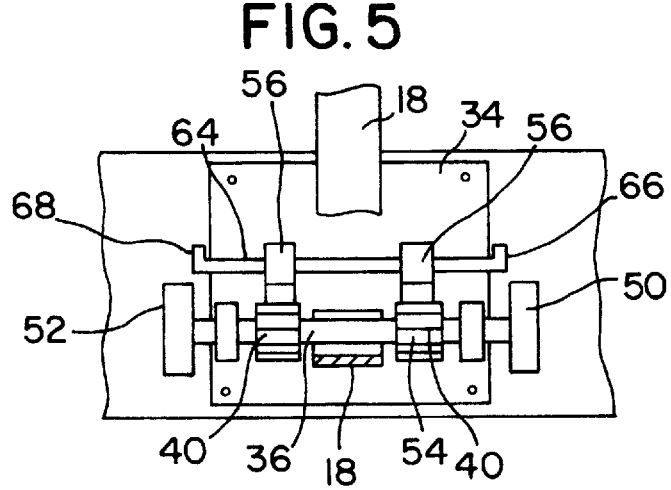
FIG. 5 is an enlarged elevation view of the tension adjusting ratchet assembly taken from the rear and with the housing cover removed.

The exercise and posture correcting device in accordance with this invention comprises an elongated biasing member 2 of spring steel or the like, secured at its lower end 4 to the rearward portion 6 of a waist belt 8 by a tensioning assembly 10. The upper end 12 of the elongated biasing member 2 includes a padded contact member 14 for contacting and bearing against a wearer's back 16 in a region substantially between the shoulder blades.

The elongated biasing member 2 in the preferred embodiment described herein comprises a slightly bowed spring steel strip 18 about three to four inches wide and about twelve inches in length from its connection to the tensioning assembly 10 at its lower end to its upper end 20. The steel strip 18 is bowed in the direction which when the exercise and posture correcting device is being worn, positions the concave surface of the bowed strip facing inwardly toward the wearer's back and positions the opposite convex surface facing outwardly away from the wearer. A height adjustable extension sleeve 22 having a receiving cavity 24 therein receives the upper end 20 of the spring steel strip 18 in such cavity 24. The padded contact member 14 is secured to the upper end 26 of the extension sleeve 22. The extension sleeve telescopes downwardly and upwardly on the spring steel strip 18 to adjust the height of the padded contact member 14 above the waist of the wearer. Thus, the exercise and posture correcting device in accordance with this invention can be used with persons of differing heights and still place the padded contact member 14 of the elongated biasing member 2 at the proper location of the wearer's back 16, substantially between the shoulder blades.

The height adjustable extension sleeve 22 is about seven inches in length, its receiving cavity 24 has a dimension and cross-sectional configuration conforming to that of the upper end portion of the spring steel strip 18 to be received therein. A set screw 28 is provided through the outwardly facing wall 30 of the sleeve 22 near its lower end 32 for tightening against the spring steel strip 18 in the cavity 24 to hold the sleeve 22 in whatever adjusted position desired, and for loosening when desired to change the height position of the padded contact member 14.

The tensioning assembly 10 comprises a steel plate 34 secured to the rearward portion 6 of the waist belt 8, on which a shaft 36 is mounted for rotation in a pair of spaced apart ratchet assemblies 40 which are riveted or otherwise secured to the steel plate 34. The lower end 42 of the slightly bowed spring steel strip 18 is wound into a coil 44. The coil end 46 is received in a slot 48 through the shaft 36 and secured therein by crimping or by other securing means. When viewed from the right hand side of a wearer, the coil 44 extends around the shaft 36 from its coil end 46 in a clockwise direction of rotation, or counterclockwise when viewed from the left hand side.

A pair of knobs 50 and 52 are secured to respective opposite ends of the shaft 36 to enable the wearer to reach behind his back to rotate the shaft 36 in a direction of rotation which increases the tension of the padded contact member 14 against his back or in the opposite direction to decrease the tension. When knob 50 on the right hand side of the wearer is rotated clockwise, the tension of padded contact member 14 against the wearer's back is increased. When it is rotated counterclockwise, the tension is decreased.

Rotation of knob 52 on the left hand side of the wearer is the reverse. Clockwise rotation of knob 52 will decrease the tension. Counterclockwise rotation of knob 52 will increase the tension. The wearer can reach behind his back to rotate both knobs 50 and 52 at the same time. The shaft 36 rotates in the same direction when knob 50 on the right hand side is rotated in the clockwise direction and knob 52 on the left hand side is rotated in the counterclockwise direction, and vice versa.

Each of the ratchet assemblies 40 are the same, so only one will be described in detail. A portion of shaft 36 which is received through each ratchet assembly 40 includes ratchet teeth 54 formed thereon. A pawl 56 is pivotally mounted in each ratchet assembly in line with the ratchet teeth 54 and its tooth contact end 58 is normally biased in the direction toward contact with the teeth 54. The pawl release end 60 of each pawl 56 extends outwardly of each ratchet assembly housing 62 of each ratchet assembly 40. A laterally extending coupling bar 64 is connected to each pawl 56 at its outwardly extending pawl release end 60. The coupling bar end 66 to the right hand side of the wearer terminates adjacent to knob 50. The coupling bar end 68 to the left hand side of the wearer terminates adjacent to knob 52.

The ratchet teeth 54 have a cam surface 70 on the side thereof which faces the clockwise direction of rotation when viewed from the wearer's right hand side, whereby the shaft 36 can be rotated without being stopped in that direction which increases the tension of the padded contact member 14 against the wearer's back. The cam surfaces 70 form an obtuse angle at their connection point to the ratchet wheel 72. The ratchet teeth 54 have an abutting surface 74 on their opposite side, which forms an acute or right angle at their connection point to the ratchet wheel 72.

When the wearer desires to increase tension of the padded contact member 14 against his back, he can reach behind his back and freely rotate knob 50 clockwise and knob 52 counterclockwise as much as necessary to reach the desired amount of tension. When he desires to decrease tension, he can reach behind his back for either the pawl release coupling bar end 66 or 68, or both, which are adjacent the respective knobs 50 and 52, and move the pawl release coupling bar in the pawl release direction. The pawl 56 is then released from contact with the ratchet teeth 54 and the shaft 36 is then free to rotate in the counterclockwise direction viewed from the right hand side of the wearer, or the tension decreasing direction. While holding the pawl release coupling bar 64 in its pawl release position with one hand on the coupling bar end 66 adjacent knob 50, the other hand can rotate knob 52 on the opposite side in the tension decreasing direction to decrease tension of the padded contact member 14 against the wearer's back to whatever extent desired.

The waist belt 8 is preferable made of leather or comparable material and is wide enough to maintain a substantially vertical position of the steel plate 34 secured thereto when the belt is tightened around the waist of the wearer and the elongated biasing member 2 carried on the steel plate 34 biases the padded contact member 14 against the wearer's back in the area between his shoulder blades. The width of the belt in the preferred embodiment described herein is about six inches, but it may be wider or narrower and still be within the scope of this invention. The belt 8 as described herein includes a pair of connecting belt straps 76 and 78 for receipt respectively in buckles 80 and 82 and buckling thereto when the belt 8 is drawn up snugly around the waist of the wearer.

The tension of the padded contact member 14 against the wearer's back in the region between his shoulder blades should be sufficient to require the wearer to exert a reverse force on such contact member 14 in order to achieve a normal upright position. Such exertion causes the muscles which control straightening a person's body to the normal upright position to become strengthened. As they do become strengthened from using the exercise and posture correcting device in accordance with this invention, the wearer can progressively increase the tension of the padded contact member 14 against his back to require progressively more reverse force to achieve and maintain the normal upright position which in turn further strengthens those muscles. Eventually, after using the exercise and posture correcting invention described herein for a sufficient length of time, a person's muscles which control straightening the body to the normal upright position will become strong enough to maintain the correct posture by themselves.

I claim:

1. An exercise and posture correcting device, comprising upper body contact means for contacting and bearing against a subject's back above the waist in the region between his shoulder blades, support means wearable about the waist of the subject; and tensioning means connected to said contact means at one end and to said support means at the other end to urge said contact means against said subject's back, the correcting device having no portion of the tensioning means extending below the support means to contact below the waist of the subject in use.

2. An exercise and posture correcting device as set forth in claim 1, wherein said tensioning means includes spring means.

3. An exercise and posture correcting device as set forth in claim 2, wherein said spring means includes a strip of metal having the flexing characteristics of spring steel.

4. An exercise and posture correcting device as set forth in claim 3, wherein said support means includes a waist belt for said subject to wear around his waist, said tensioning means extends upwardly between said waist belt and said contact means, said tensioning means includes height adjusting means to adjust the distance said contact means extends above said waist belt.

5. An exercise and posture correcting device, comprising contact means for contacting and bearing against a subject's back in the region between his shoulder blades, tensioning means connected to said contact means to urge said contact means against said subject's back in said region, and support means wearable by said subject for supporting said contact means and said tensioning means, wherein said tensioning means includes spring means, wherein said spring means includes a strip of metal having the flexing characteristics of spring steel, wherein said support means includes a waist belt for said subject to wear around his waist, said tensioning means extends upwardly between said waist belt and said contact means, said tensioning means includes height adjusting means to adjust the distance said contact means extends above said waist belt, wherein said height adjusting means includes a sleeve member having an insert receiving cavity therein, said strip of metal having an upper free end and an opposite lower end, said upper free end of said strip of metal being received in said insert receiving cavity of said sleeve member, said sleeve member being slidable on said strip of metal received in said cavity between a lowest position and a highest position, and releasable securing means to releasably secure said sleeve member to said strip of metal at any desired position of adjustment between said lowest position and said highest position, said sleeve member having an upper end, said tensioning means being connected to said contact means at said upper end of said sleeve member.

6. An exercise and posture correcting device as set forth in claim 5, wherein said releasable securing means to releasably secure said sleeve member to said strip of metal includes a set screw.

7. An exercise and posture correcting device as set forth in claim 5, wherein said contact means includes a padded contact member.

8. An exercise and posture correcting device as set forth in claim 5, wherein said support means includes a rigid plate secured to said waist belt.

9. An exercise and posture correcting device as set forth in claim 8, wherein said tensioning means includes connecting means for connecting said lower end of said strip of metal of said tensioning means to said rigid plate.

10. An exercise and posture correcting device as set forth in claim 9, wherein said connecting means includes tension increasing means for increasing the pressure of said contact member against said back of said subject.

11. An exercise and posture correcting device as set forth in claim 10, wherein said tension increasing means includes a ratchet assembly secured to said rigid plate secured to said waist belt.

12. An exercise and posture correcting device as set forth in claim 11, wherein said ratchet assembly includes a rotatable shaft mounted for rotation thereon in a tension increasing direction of rotation and in the opposite tension decreasing direction, said lower end of said strip of metal being secured to said rotatable shaft whereby said strip of metal, said sleeve member thereon and said contact member are more strongly urged in the direction toward said back and shoulder blade area of said subject when said shaft is rotated in said tension increasing direction, ratchet teeth around a portion of said rotatable shaft, a pawl mounted on said ratchet assembly for operative engagement with said ratchet teeth to permit said shaft to rotate in said tension increasing direction and to hold said shaft from rotation in the opposite direction, a release member to disengage said pawl from operative engagement with said ratchet teeth to thereupon permit said shaft to rotate in said opposite tension decreasing direction, and shaft operating means to rotate said shaft.

13. An exercise and posture correcting device as set forth in claim 12, wherein said shaft operating means includes a knob for said subject to grasp and rotate said shaft by hand.

14. An exercise and posture correcting device as set forth in claim 12, wherein said rotatable shaft is elongated and extends laterally from a first end on one side of said ratchet assembly to a second end on the other side thereof, said shaft operating means includes a first knob on said first end of said rotatable shaft and a second knob on said second end of said rotatable shaft.

15. An exercise and posture correcting device as set forth in claim 14, wherein said release member to disengage said pawl from operative engagement with said ratchet teeth includes a laterally extending operating bar connected to said release member, said laterally extending operating bar terminating on one side in a first bar end adjacent said first knob and terminating on the other side in a second bar end adjacent said second knob whereby said pawl can be released by moving said operating bar at either said first or second bar end in the direction which causes said release member to disengage said pawl from operating engagement with said ratchet teeth.

16. An exercise and posture correcting device as set forth in claim 14, wherein said strip of metal of said tensioning means includes a coil in a portion thereof extending from said lower end thereof connected to said rotatable shaft in the direction toward said opposite upper end of said strip of metal.

* * * * *